United States Patent [19]
Eckenhoff et al.

[11] Patent Number: 4,772,474
[45] Date of Patent: * Sep. 20, 1988

[54] DISPENSER WITH INTERNAL ARRANGEMENT OF LAMINA MEANS FOR DISPENSING BENEFICIAL AGENT

[75] Inventors: James B. Eckenhoff, Los Altos; Richard Cortese, Los Gatos; Felix A. Landrau, Milpitas, all of Calif.

[73] Assignee: ALZA Corporation, Palo Alto, Calif.

[*] Notice: The portion of the term of this patent subsequent to Jun. 12, 2003 has been disclaimed.

[21] Appl. No.: 895,613

[22] Filed: Aug. 11, 1986

Related U.S. Application Data

[60] Division of Ser. No. 764,143, Aug. 9, 1985, Pat. No. 4,624,945, which is a continuation-in-part of Ser. No. 590,778, Mar. 19, 1984, Pat. No. 4,595,583.

[51] Int. Cl.[4] .......................... A61K 9/22; A61K 9/44; A01N 25/26; A61J 3/00
[52] U.S. Cl. .................................... 424/465; 424/476; 424/438; 604/892.1
[58] Field of Search .............................. 604/890–895, 604/8–10; 514/962; 424/14–16, 19–21, 420, 438, 422, 465, 476

[56] References Cited

U.S. PATENT DOCUMENTS

| | | | |
|---|---|---|---|
| 3,594,469 | 7/1971 | Whitehead et al. | 424/22 |
| 3,732,865 | 5/1973 | Higuchi et al. | 604/892 |
| 3,995,632 | 12/1976 | Nakano et al. | 604/892 |
| 4,327,725 | 5/1987 | Cortese et al. | 604/893 |
| 4,475,916 | 10/1984 | Himmelstein | 604/890 |
| 4,595,583 | 6/1986 | Eckenhoff et al. | 604/890 |
| 4,612,008 | 9/1986 | Wong et al. | 604/890 |
| 4,645,502 | 2/1987 | Gale et al. | 604/896 |

Primary Examiner—C. Fred Rosenbaum
Assistant Examiner—Sharon Rose
Attorney, Agent, or Firm—Paul L. Sabatine; Edward L. Mandell; Steven F. Stone

[57] ABSTRACT

A dispensing system is disclosed comprising a wall surrounding a lumen. The lumen comprises (1) a thermo responsive composition comprising a beneficial agent, (2) means for occupying space in the lumen for pushing the thermo responsive composition from the dispensing system, and (3) means for enhancing the amount of the beneficial agent dispensed from the system positioned between the thermo responsive composition and the means for occupying space.

18 Claims, 7 Drawing Sheets

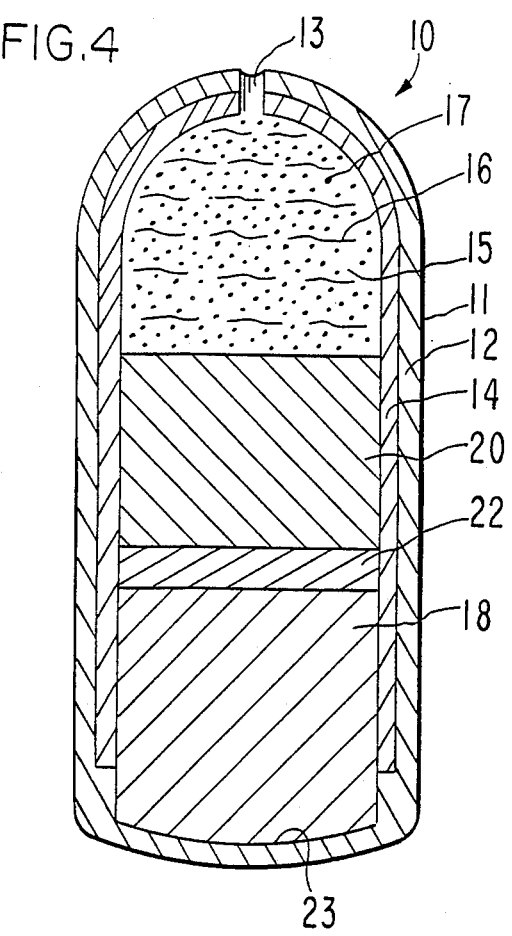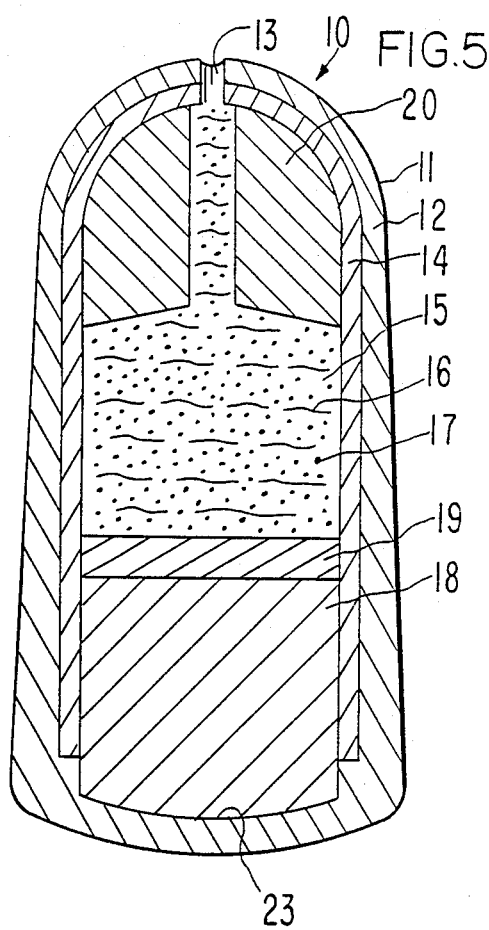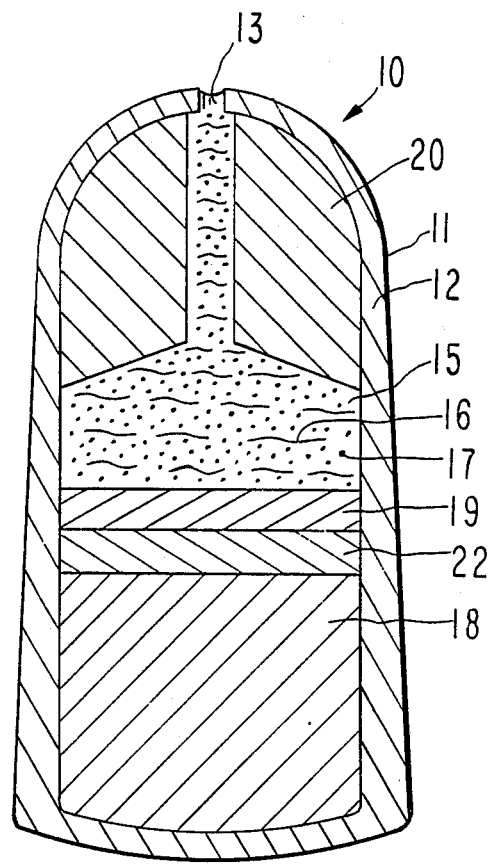

DISPENSER WITH INTERNAL ARRANGEMENT OF LAMINA MEANS FOR DISPENSING BENEFICIAL AGENT

CROSS-REFERENCE TO RELATED APPLICATIONS

This application is a division of U.S. patent application Ser. No. 06/764,143 filed Aug. 9, 1985 now U.S. Pat. No. 4,624,945 issued on Nov. 25, 1986 which U.S. application Ser. No. 06/764,143 is a CIP of U.S. application Ser. No. 06/590,778 filed Mar. 19, 1984 now U.S. Pat. No. 4,595,583 issued June 17, 1986. These applications are assigned to ALZA Corporation of Palo Alto, Calif., and benefit is claimed of their filing dates.

FIELD OF THE INVENTION

This invention pertains to both a novel and useful dispensing system. More particularly, the invention pertains to a dispenser comprising a wall that surrounds an inner space housing comprising (1) a thermo-responsive beneficial agent formulation, (2) an expandable driving member, (3) means positioned between the thermo-responsive beneficial agent formulation and the expandable means for increasing the amount of beneficial agent formulation dispensed from the system, and (4) optionally, a density member. The components comprising the dispensing system perform together in harmony for delivering the beneficial agent formulation at a controlled rate to a fluid, thermal environment of use over a prolonged period of time. The invention pertains also to laminated structures used for manufacturing the dispensing system, to compositions of matter, and to a method for administering a beneficial agent using the dispenser.

BACKGROUND OF THE INVENTION

There has long been a pressing need in the medical, pharmaceutical and veterinary arts for a dispensing system that is capable of administering a beneficial agent at a controlled rate over a prolonged period of time. The need exists for increasing the maximum time of therapeutic effectiveness of beneficial agents, especially for beneficial agents whose maximum time of therapeutic effectiveness, when administered in conventional dosage forms such as a tablet, is only for a few hours. A patient using such a conventional form must take repeated dosages at frequent intervals. Moreover, during intervals between doses the therapeutic level in the blood decreases due to metabolic activities and the level can become so low that it is practically ineffective. Also, as a result of frequent doses, the level of medicine available for therapy will fluctuate between doses. The need for a dispenser exists also for delivering beneficial agents that are difficult to deliver, usually attributable to some physical property. For example, beneficial agents that are insoluble in aqueous fluids are difficult to deliver because they do not form solutions and, accordingly, they cannot be dispensed in solution from a dispensing device. Then, too, many beneficial agents exhibit lipid solubilities and these agents are difficult to deliver by conventional dosage forms.

Additionally, a need exists for a dispensing system for dispensing a beneficial agent to a ruminant animal. Ruminant animals, including cattle, sheep, giraffe, deer, goat, bison and camels, and more particularly cattle and sheep, comprise an important group of animals that require periodic administration of beneficial agents and nutrients. The beneficial agents and nutrients are administered for better health and for the treatment and alleviation of various conditions. Ruminants have a complex three or four compartment stomach. The rumen, the largest of the stomach compartments, serves as an important location for receiving and passing beneficial agents and nutrients into other compartments, including the abomasum and the intestine.

Presently ruminants are treated by repeated administrations of agents and nutrients at frequent time intervals. This form of treatment is inconvenient and expensive, and it does not lend itself to good reliable therapy or nutrition. Additionally, agents and nutrients are orally administered in the form of a bolus to ruminants, and this form of administration, like other repeated modes of administration, also does not lend itself to acceptable therapy or nutrition. Moreover, ruminants regurgitate what they swallow, they chew their cuds, and they spit out conventional boluses quickly after administration thereof.

There is therefore, in view of the above presentations, a pressing need for a dispensing system for use with ruminants that will, after a single administration, efficiently administer agents and nutrients over a prolonged period of time. There also is a pressing need for a dispensing system for a prolonged release of an agent or a nutrient at a controlled rate in the rumen, by a dispensing system that is swallowed easily by the ruminant and will remain in the rumen for a long period of time without being regurgitated or otherwise eliminated from the rumen.

OBJECTS OF THE INVENTION

It is a principle object of this invention to provide both a novel and useful dispensing system for dispensing a beneficial agent, including nutrient, which dispensing system fulfills the pressing need known to the prior art.

It is another object of this invention to provide a dispensing system that can deliver a beneficial agent at a controlled rate over a prolonged period of time, thereby overcoming the shortcomings associated with the prior art dosage forms.

It is another object of the invention to provide a dispensing system manufactured as a dispenser that is self-contained, self-starting and self-powered in a fluid environment of use for dispensing a beneficial agent to the environment of use, including a warm-blooded animal.

It is another object of the invention to provide a dispensing system comprising wall means that surrounds and forms a lumen comprising a heat sensitive means containing a beneficial agent, a driving means for delivering the beneficial agent from the dispensing system, and means for increasing the amount of beneficial agent delivered from the dispensing system.

It is another object of the invention to provide a dispensing system comprising (1) a wall comprising in at least a part of a composition permeable to the passage of fluid, (2) an internal lumen housing (3) a thermo-sensitive composition containing a beneficial agent, (4) an expandable member, and (5) a member for increasing the amount of agent delivered, for enhancing the delivery profile, and for protecting the agent, and which dispensing system delivers the beneficial agent by the combined physical-chemical operations of the composition melting or undergoing dissolution to become fluid, semisolid or the like, the expandable member swelling and occupying space in the area previously occupied by the composition, with the member increasing the amount of beneficial agent delivered, thereby dispensing the beneficial agent through means in the wall for delivering the beneficial agent over time.

It is another object of this invention to provide a dispersing system that delivers a beneficial agent contained in a thermo-responsive, lipophilic pharmaceutical acceptable carrier that softens in the presence of thermal energy absorbed from the environment of use and thereby forms a dispensable composition that is innocuous and can be dispensed from the dispensing system over time.

It is another object of this invention to provide a dispensing system containing an eutectic composition comprising at least two components and at least one beneficial agent, which eutectic composition has a melting point approximately the same as the temperature of the warmblooded animal recipient plus or minus a few degrees thereof, and is dispensed from the dispensing system at said temperature.

It is another object of this invention to provide a dispensing system comprising an inner positioned capsule housing thermo-responsive hydrophobic composition comprising from insoluble to soluble agents such as drugs, and which thermo-responsive composition, in response to energy input present in the biological environment of use, changes its form and becomes dispensable for operative delivery from the dispensing system.

It is another object of this invention to provide a dispensing system comprising a capsule containing a temperature-sensitive composition, an expandable member, and a densifier in parallel arrangement, an outer wall comprising totally or in part a semipermeable composition surrounding the capsule, and a dispensing passageway useful for dispensing a beneficial agent to an animal.

It is another object of this invention to provide a dispensing system that can remain in the rumen of a ruminant for a prolonged period of time.

It is another object of this invention to provide a dispenser for use in animals, including ruminants, that delivers a beneficial agent including medicines and nutrients, and which dispenser is easy to manufacture at a lesser cost thereby increasing the usefulness of the dispenser for administering the agent over a prolonged period of time.

It is another object of the invention to provide a dispenser comprising a dense member for keeping the dispenser in the rumen over time, wherein the dispenser delivers a composition that is a complete pharmaceutical dosage regimen for a prolonged period of time, the use of which dispenser requires intervention only for the initiation of the regimen.

It is another object of this invention to provide a composition of matter comprising a beneficial agent and a heat sensitive composition useful for manufacturing a dispensing device.

It is another object of this invention to provide a dispensing system for dispensing a beneficial agent to an animal, including a human, which dispensing system comprises an inner capsule body containing a thermoplastic composition and an expandable composition, and a dense member when the dispensing system is used with a ruminant, and which composition includes a beneficial agent that is insoluble or soluble in an aqueous environment and can be housed in the dispensing system in a nonaqueous carrier that can be delivered to an animal.

Other objects, features and advantages of the invention will be more apparent to those skilled in the dispensing art from the following detailed description of the specification, taken in conjunction with the drawings and the accompanying claims.

BRIEF DESCRIPTION OF THE DRAWINGS

In the drawings, which are not drawn to scale, but are set forth to illustrate various embodiments of the invention, the drawing figures are as follows:

FIG. 4 is an opened view of the dispensing system depicting a wall comprising in at least a part a semipermeable composition surrounding a lumen with the dispensing system comprising all the elements set forth above designed to act in concert for the controlled delivery of a beneficial agent over time;

FIG. 5 is an opened view of the dispensing system depicting a wall comprising in at least a part a semipermeable composition surrounding a lumen comprising the elements as set forth above with the system housing, additionally, a first and second lamina for enhancing the dispensing ability of the system.

FIG. 6 is an opened view of a dispensing system provided by the invention depicting a different internal structural configuration of the internal elements comprising the dispensing system and the exterior wall of varying thickness which wall increases in thickness from its lead end to its terminal end;

Figure 2:
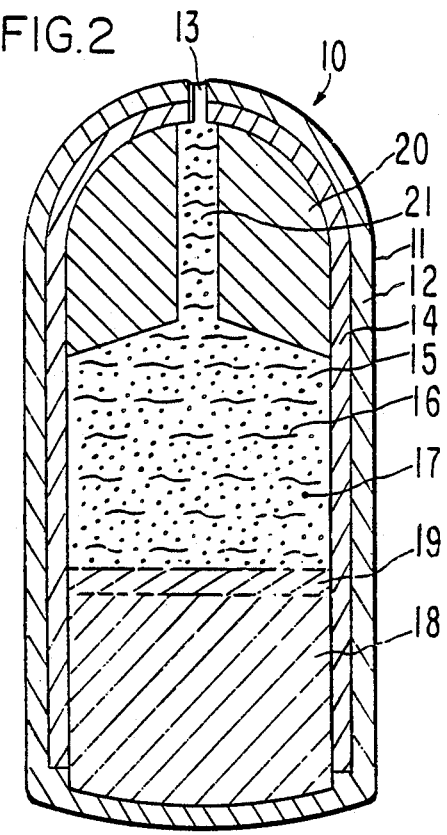
FIG. 2 is an opened view of the dispensing system of FIG. 1, for illustrating the structure of the dispensing system comprising an outside wall, an inside wall, a thermo-responsive composition, an expandable member, a dense member, and a member for assuring the release of agent from the dispensing system.

The laminates of FIGS. 14 through 17 are prepared by following the teachings of the specification for example, as see but not limited to, FIG. 2, Examples 1, 9 and 12 and the like.

In the drawings and in the specifications, like parts in related figures are identified by like parts. The terms appearing earlier in the specifications and in the description of the drawing figures, as well as embodiments thereof, are further detailed elsewhere in the disclosure.

DETAILED DESCRIPTION OF THE DRAWING FIGURES

Figure 1:
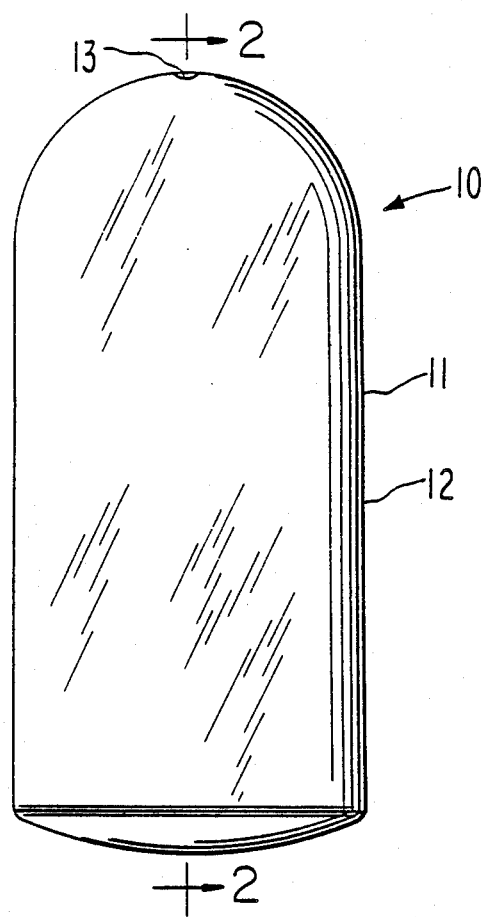
FIG. 1 is a view of a dispensing system designed for orally administering a beneficial agent to a warm-blooded animal.

Turning now to the drawing figures in detail, which are examples of a new and useful beneficial dispensing system, and which examples are not to be construed as limiting, one example of a dispenser is depicted in FIG. 1, identified by the numeral 10. In FIG. 1, dispenser 10 comprises a body 11 formed of wall means 12 that surrounds and defines an internal lumen, not seen in FIG. 1. Dispensing system 10 comprises agent exit means 13, indicated by a partial hole in FIG. 1, for dispensing a beneficial agent formulation from dispensing system 10.

FIG. 2 is an opened view of beneficial dispensing system 10 of FIG. 1. Beneficial system 10 of FIG. 2 comprises body 11, wall means 12 and dispensing exit means 13. Wall 12 surrounds an internal capsule wall 14 and internal compartment or lumen 15. Wall 12 comprises, in a presently preferred embodiment, a semipermeable wall forming composition that is substantially permeable to the passage of an external fluid, and it is substantially impermeable to the passage of a beneficial agent and other ingredients contained in dispensing system 10. In another embodiment wall 12 can be formed of a semipermeable composition that partly surrounds the capsule and the rest of wall 12 can comprise a different wall forming composition. Wall 12 is non-toxic, it is inert, and it maintains its physical and chemical integrity, that is, it doesn't erode during the dispensing period. System 10, in one presently preferred embodiment, comprises internal wall 14 made in its final manufacture as a single unit capsule body member. In FIG. 2, capsule wall 14 surrounds lumen 15. Lumen 15 contains a thermo-responsive heat sensitive composition 16, identified by wavy lines, containing a beneficial agent 17, represented by dots. Lumen 15 further contains an expandable driving means 18 that is separated from thermo-responsive heat composition 16 by lamina 19. Lamina 19 is positioned between the active formulation 16 and the expandable driving member 18 for substantially reducing diffusion, migration, entrapment or the like of active agent 17 into expandable member 18. Lamina 19 also protects active agent formulation 16 from possible interaction with expandable member 18 thereby improving the stability of agent formulation 16. Additionally, in one presently preferred embodiment, lamina 19 is made from a soft or flexible polymer composition for aiding in pushing the maximum amount of formulation 16 containing agent 17, from system 10 as formulation 16 contacts density member 20. Thermo-responsive composition 16 and expandable member 18 have a shape that corresponds to the internal shape of capsule wall 14 and lumen 15. Lumen 15 also contains a dense member 20 or densifier that is in contact with thermo-responsive composition 16, which dense member 20 is positioned in lumen 15 distant from expandable member 18. A means 13, illustrated in this embodiment as a passageway 13, extends through wall 12, inner capsule 14, for connecting the exterior of dispenser 10 with the interior of dispenser 10, mainly lumen 15. Dense member 20 has a bore 21 therethrough for dispensing composition 16 from lumen 15 to exit passageway means 13 for release from dispenser 10. Dense member 20 is an important component of delivery system 10 optionally present and used for keeping dispenser 10, when in use, in the rumen of an animal over a prolonged period of time.

Figure 3:
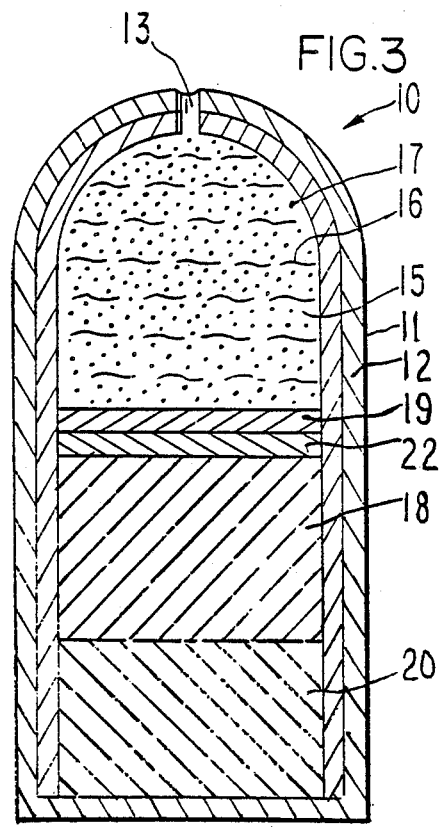
FIG. 3, is an opened view of FIG. 1, opened through the vertical length of the dispensing system, for illustrating another embodiment comprising a first and second lamina for enhancing the effectiveness of the dispensing system.

FIG. 3 depicts another manufacture provided by the invention. FIG. 3 is an opened view of the dispensing system 10 of FIG. 1, and it comprises body 11, an exterior wall 12 of uniform thickness, internal wall 14, internal compartment 15, and exit means 13. System 10 further comprises a thermo-responsive heat composition 16 containing beneficial agent 17. Thermo-responsive heat composition 16 is, in this manufacture, immediately to exit means 13. Compartment 15 also contains an expandable driving member 18 separated by first lamina 19 and second lamina 22 from thermo-responsive composition 16. Driving member 18 is in laminar arrangement with, and positioned adjacent to dense member 20. Dense member 20, in FIG. 3, is positioned distant from exit means 13. In FIG. 3, dispenser 10 additionally comprises lamina 22. Lamina 22 is preferably formed of an impervious and rigid material for lessening the incidence of undesirable contamination in compartment 15. Lamina 22 also is a means for increasing the delivering efficiency of dispenser 10, by insuring the total force generated by expandable member 18 is applied against heat-responsive formulation 16, containing agent 17, for squeezing formulation 16 through exit means 13. Lamina 22 functions like a piston and it is so constructed as to moveably provide and maintain a tight piston-head arrangement between the active agent phase and the expandable phase in compartment 15. Lamina 22 is frictionally disposed, but it is free to move within dispenser 10 by sliding while at the same time maintaining the operability of dispenser 10.

FIG. 4 depicts another embodiment provided by the invention. FIG. 4 is an opened view of dispensing system 10 comprising body 11, exterior wall 12, that surrounds interior wall 14. Interior wall 14 partially surrounds internal compartment 15 and it is provided with an opened end or mouth 23, at the end of device 10. Mouth 23 is a means for providing easy access to internal lumen 15 for placing therein thermo-responsive composition 16 containing beneficial agent 17, density member 20, optional lamina 22 and expandable driving member 18. Lamina 22 transmits the full driving force of expanding member 18 against density member 20 for urging thermo-responsive composition 16 containing beneficial agent 17 through exit means 13 from dispenser 10.

FIG. 5 depicts another embodiment provided by the invention. FIG. 5 is an opened view of dispensing system 10 comprising body 11, exterior wall 12 that surrounds interior wall 14. Interior wall 14 partially surrounds internal compartment 15 except for mouth 23. Dispensing device 10 provides a different internal arrangement exemplified by dense member 20 immediately adjacent to exit means 13, heat-responsive composition 16 containing beneficial active agent 17 in contacting arrangement with density member 20, first lamina 19 in laminar arrangement with heat-sensitive composition 16 and expandable member 18 in laminar arrangement with the free face of lamina 19. Additionally, exterior wall 12 increases in thickness from the dispensing end to the terminal end of the device.

FIG. 6 depicts another embodiment provided by the invention. FIG. 6 is an opened view of dispensing system 10 comprising a wall 12 surrounding an internal compartment 15 housing dense member 20, heat-responsive composition 16 containing beneficial agent 17, first lamina 19 in laminar arrangement with second lamina 22 and expandable member 18.

Figure 7:
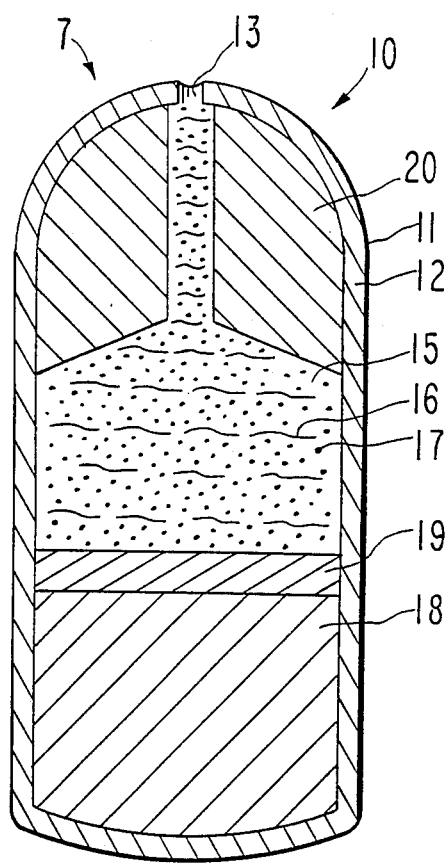
FIG. 7 is an opened view of a dispensing system provided with a different internal arrangement of the internal members comprising the dispensing system.

FIG. 7 depicts another embodiment provided by the invention, seen in opened view. Dispensing system 10 in this embodiment comprises, in internal compartment 15, density member 20, heat responsive composition 16 comprising beneficial agent 17, first lamina 19 and expandable member 18.

Figure 8:
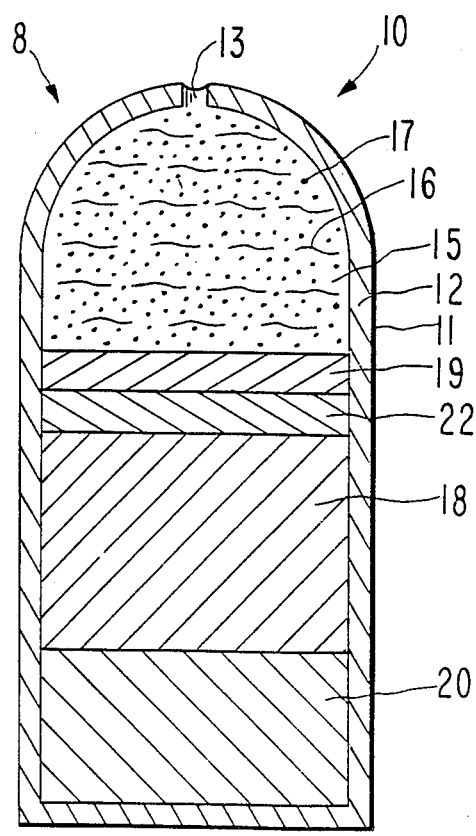
FIG. 8 is an opened view of the dispensing system of FIG. 7 illustrating the system with a single wall and a pair of internal members in operation delivering a beneficial agent over time.

FIG. 8 depicts another embodiment provided by the invention, seen in opened section. Dispensing system 10 in this embodiment comprises wall 12 surrounding internal compartment 15 housing next to exit means 13 heat-sensitive composition 16 containing beneficial agent 17 in contacting position with first lamina 19 and second lamina 22, expandable member 18 and density member 20 at the trailing end of dispenser 10.

Figure 9:
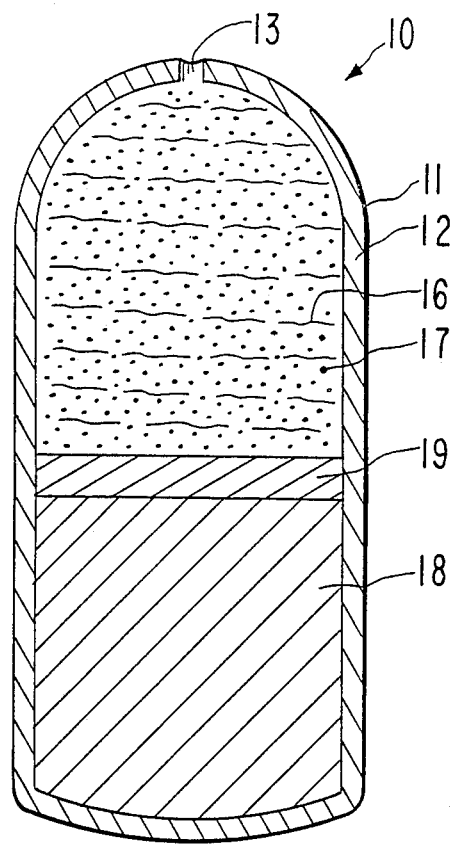
FIG. 9 is an opened view of another embodiment of the dispensing system comprising a wall surrounding an internal lumen housing a heat sensitive formulation, an expandable member and a lamina position between the heat sensitive formulation and the expandable member, and which dispensing system optionally omits a density member.

FIG. 9 depicts another embodiment provided by the invention. In FIG. 9, dispensing device 10 is illustrated in opened section and it comprises body 11, wall 12 that surrounds and forms an internal compartment 15. Wall 12 comprises, in a presently preferred embodiment, a semipermeable wall forming composition that is permeable to the passage of an external fluid and it is substantially impermeable to the passage of a beneficial agent and other ingredients present in compartment 15. Internal compartment 15 contains heat-sensitive, thermo-responsive composition 16, homogeneously or heterogeneously containing beneficial agent 17. Compartment 15 further contains expandable driving member 18, that is separated from heat-sensitive composition by lamina 19 positioned there between. Lamina 19 comprises a polymeric composition that lessens intermixing of heat-sensitive composition 16 and expandable member 18 and it is preferably flexible and adopts the internal shape of compartment 15. Dispensing device 10 of FIG. 9 is manufactured without a density member and it is sized and shaped for preferable use in a non-ruminant, such as the body passageway of a warm-blooded animal.

Figure 10:
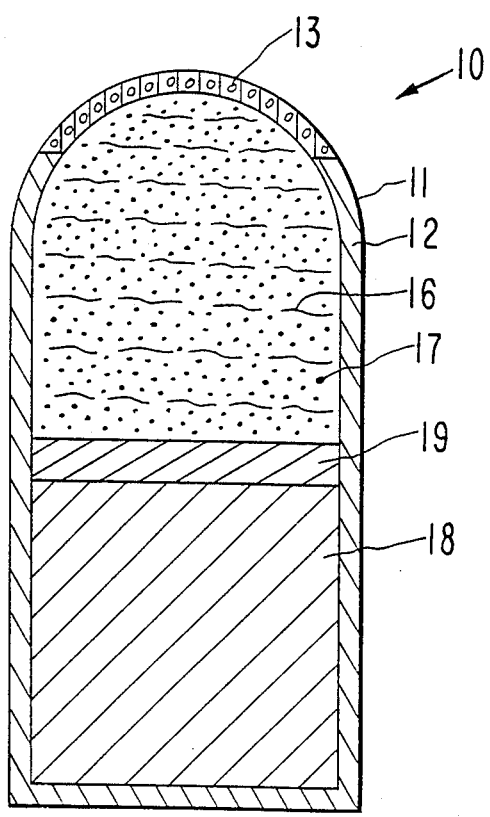
FIG. 10 is an opened view of a dispensing system similar to the dispensing system of FIG. 9, with the dispensing system of FIG. 10 embodying more than one passageway for releasing a beneficial agent formulation from the system.

FIG. 10 depicts another embodiment provided by the invention. In the embodiment depicted in FIG. 10, wall 12 comprises in at least a part a semipermeable composition, with the remainder of wall 12 comprising a wall forming composition that is an exit means 13 for releasing beneficial agent 17 from dispensing system 10. In FIG. 10, exit means 13 comprises a microporous element comprising at least one pore that is a passageway for releasing beneficial agent 17 from dispensing system 10.

Figure 11:
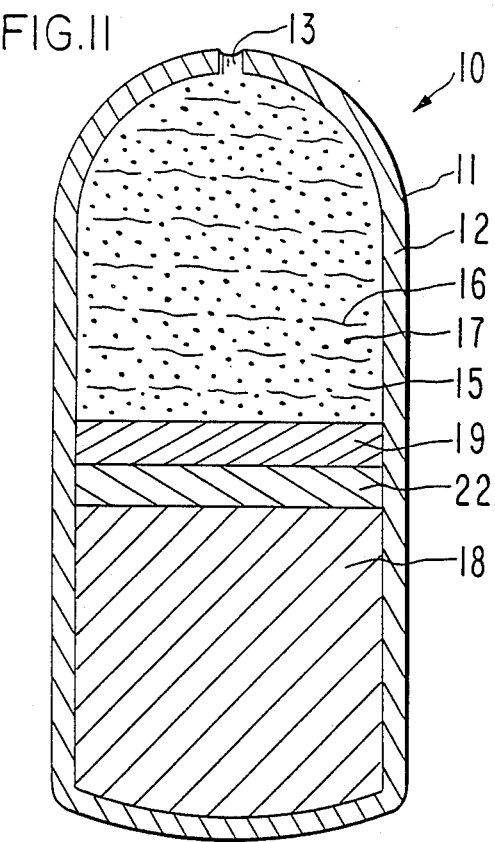
FIG. 11 is an opened view of a dispensing system similar to the dispensing system of FIG. 9 with the dispensing system of FIG. 11 housing a first and second lamina.

FIG. 11 depicts another embodiment provided by the invention. In FIG. 11 dispensing device 10 is similar to device 10 of FIG. 9, with the added feature that in FIG. 11 device 10 additionally comprises interposed second lamina 22.

Figure 12:
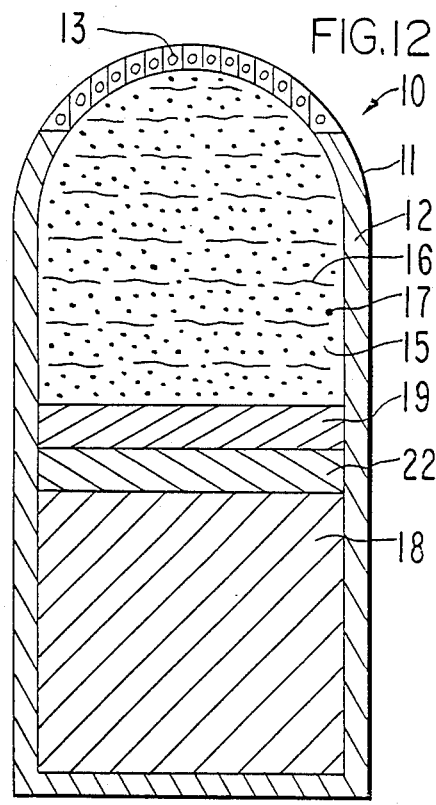
FIG. 12 is an opened view of a dispensing system similar to FIG. 10 with the dispensing system of FIG. 12 housing a first and second lamina.

FIG. 12 depicts another embodiment provided by the invention. In FIG. 12, dispensing device 10 is similar to device 10 of FIG. 10, with the added structural embodiment in FIG. 12 of interposed second lamina 22.

Figure 13:
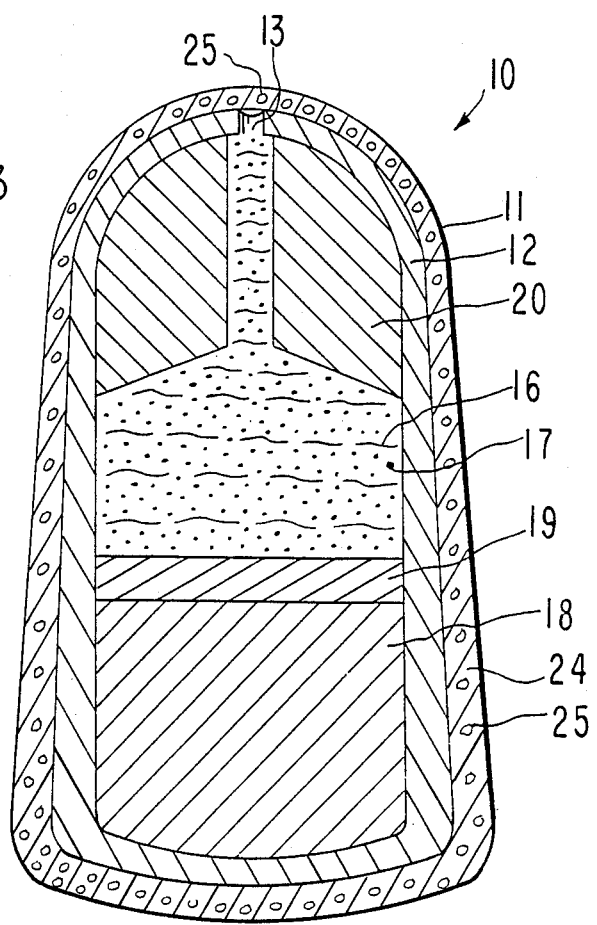
FIG. 13 is an opened view of a dispensing system comprising an exterior microporous wall that provides structural support for the system with the pores of wall a means for releasing a beneficial agent from the system.
Figure 14:
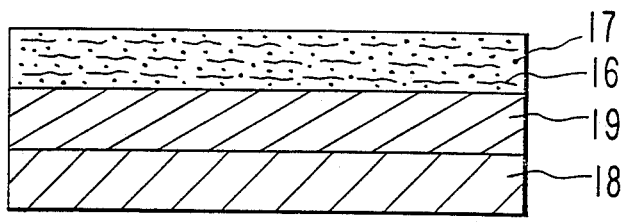
FIG. 14 illustrates a cross-section of a laminate provided by the invention comprising a heat-responsive lamina, an intermediate lamina for keeping the integrity of the laminate, and an expandable lamina.
Figure 15:
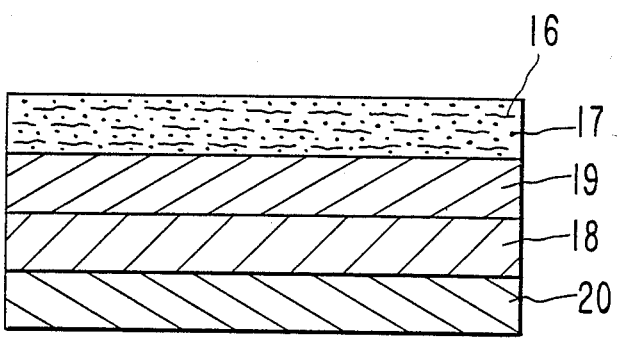
FIG. 15 illustrates a cross-section of a laminate comprising a heat-sensitive lamina, an intermediate lamina for maintaining the integrity of the laminate, an expandable lamina, and a dense lamina for keeping the device housing the laminate in an environment of use.
Figure 16:
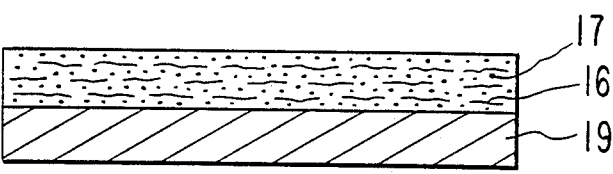
FIG. 16 illustrates a cross-section of a laminate comprising a heat-sensitive lamina and a lamina comprising a member selected from the group consisting of an ester of a fatty acid and an alcohol, a fatty acid and an alcohol, a saturated hydrocarbon.
Figure 17:
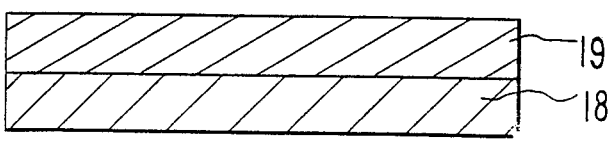
FIG. 17 illustrates a lamina comprising a hydrogel in laminar arrangement with a lamina comprising an ester of a fatty acid and an alcohol, a fatty acid and an alcohol, or a saturated hydrocarbon.

FIG. 13 depicts device 10 for dispensing beneficial agent 17 wherein device 10 comprises an exterior microporous wall forming composition 24. Wall 24 contains a pore forming agent that is removed by eroding, leaching or the like, in the environment of use to form at least one pore 25. In another manufacture, microporous wall 24 is preformed and it consists of a plurality of micropores. In either embodiment, the pores 25 are a means for releasing beneficial agent 17, received from passageway 13, from device 10.

Dispensing device 10 of FIGS. 1 through 13, when in operation, delivers beneficial agent formulation 17 to an animal fluid environment of use by a combination of thermodynamic and kinetic integrally performed activities. That is, in operation, heat-sensitive, thermo-responsive composition 16 in response to the temperature of an animal recipient absorbs thermal energy, melts, or softens, or undergoes dissolution or forms a semipaste-like composition for delivering beneficial agent 17 through exit means 13. As composition 16 absorbs thermal energy and undergoes change, concomitantly external fluid enters dispenser 10 through a fluid permeable component of wall 12 and is absorbed or imbibed by expandable hydrophilic layer 18. External fluid is imbibed by hydrophilic layer 18 to continuously expand and swell causing it to increase in volume thereby urging it against first lamina 19 and against first lamina 19 and second lamina 22. As expanding layer 18 occupies space in compartment 15 it urges the lamina to move against composition 16 containing agent 17 and, hence, through means 13 to the exterior of dispensing system 10. Further in operation, in the dispensing systems comprising an inner capsule wall when formed of an erodible, dissolvable, or the like, material, the inner thin-walled water soluble capsule member dissolves at a body temperature of 37° C. or are, leaving dispensing device 10 with outer wall 12. The dissolved wall, usually formed of gelatin, or of a gelatin blend, mixed with composition 16, and it can also lubricate the inside of surface of wall 12.

While FIGS. 1 through 13 are illustrative of various dispesing systems 10 that can be made according to the invention, it is to be undestood these devices are not to be construed as limiting the invention, as dispenser 10 can take a wide variety of shapes, sizes and forms for delivering agent 17 to the environment of use. For example, delivery device 10 can be designed for oral use for releasing a locally or a systemically acting agent in the gastrointestinal tract over time. An oral dispensing system can have various shapes and sizes such as round with a diameter of ⅛ inch to 15/16 inch, or it can be shaped like a capsule having a range of sizes from triple zero to zero and from 1 to 8. Also, dispensing device 10 can be adapted, shaped, sized and structured as a buccal, cervical, intrauterine, rectal, vaginal, nasal, dermal, subcutaneous and artificial gland device. The dispensing device can be used for administering a beneficial agent to animals, including warm-blooded mammals, humans, avians, reptiles and pisces. The dispensing device can be used in hospitals, clinics, nursing homes, farms, zoos, veterinary clinics, sickrooms, and other environments of use. The dispensing device also can be used in non-medical applications, such as agricultural, etc.

DETAILED DESCRIPTION OF THE INVENTION

In accordance with the practice of this invention, it has now been found that wall 12 can be manufactured of a wall forming composition that does not adversely affect agent 17, an animal or other host, and it is permeable in total or in at least a part to the passage of an external aqueous-type fluid, such as water and biological fluid, while remaining essentially impermeable to the passage of agents, including drugs, and the like. Typical materials for forming a semipermeable wall 12 include semipermeable polymers known to the art as osmosis and reverse osmosis membranes. These materials comprise semipermeable homopolymers, semipermeable copolymers, and the like. In one embodiment typical materials include cellulose esters, cellulose monoesters, cellulose diesters, cellulose triesters, cellulose ethers, and cellulose ester-ethers, mixtures thereof, and the like. These cellulosic polymers have a degree of substitution, D.S., on their anhydroglucose unit from greater than 0 up to 3, inclusive. By degree of substitution is meant the average number of hydroxyl groups originally present on the anhydroglucose unit that are replaced by a substituting group, or converted into another groups. The anhydroglucose unit can be partially or completely substituted with groups such as acyl, alkanoyl, aroyl, alkyl, alkenyl, alkoxy, halogen, carboalkyl, alkylcarbamate, alkylcarbonate, alkylsulfonate, aklylsulfamate, and like semipermeable polymer forming groups.

The semipermeable materials typically include a member selected from the group consisting of cellulose acylate; cellulose diacylate; cellulose triacylate; cellulose acetate; cellulose diacetate; cellulose triacetate; mono-, di- and tri-cellulose alkanylates; mono-, di- and trialkenylates; mono-, di- and tri-alkenylates; mono-, di- and tri-aroylates and the like. Exemplary polymers including cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a D.S. of 2 to 3 and an acetyl content of 34 to 44.8% and the like. More specific cellulosic polymers include cellulose propionate having a D.S. of 1.8 and a propionyl content of 30.5%; cellulose acetate propionate having an acetyl content of 1.5 to 7% and an acetyl content of 39 to 45%; cellulose acetate propionate having an acetyl content of 2.5 to 3% an average propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate; cellulose propionate morpholibnobutyrate; cellulose acetate butyrate; cellulose acetate phthalate, and the like; mixed cellulose esters such as cellulose acetate valerate; cellulose acetate succinate; cellulose propionate succinate; cellulose acetate octanoate; cellulose valerate palmitate; cellulose acetate heptonate, and the like. Semiprmeable polymers are known in U.S. Pat. No. 4,077,407, and they can be made by procedures described in *Encyclopedia of Polymer Science and Technology*, Vol. 3, pp 325–354, 1964, published by Interscience Publishers, Inc., New York.

Additional semipermeable polymers that can be used for their wall-forming properties include cellulose acetaldehyde dimethyl cellulose acetate; cellulose acetate ethylcarbamate; cellulose acetate methylcarbamate; cellulose dimethylaminoacetate; a cellulose composition comprising cellulose acetate and hydroxypropyl methylcellulose; a composition comprising cellulose acetate and cellulose acetate butyrate; a cellulose composition comprising cellulose acetate butyrate and hydroxypropyl methylcellulose; semipermeable polyamides; semipermeable polyurethanes; semipermeable polysulfanes; semipermeable sulfonated polystyrenes, cross-linked, selectively semipermeable polymers formed by the coprecipitation of a polyanion and a polycation as disclosed in U.S. Pat. Nos. 3,173,876; 3,276,586; 3,541,005; 3,641,006, and 3,546,142; selectively semipermeable silicon rubbers; semipermeable polymers as disclosed by Loeb and Sourirajan in U.S. Pat. No. 3,133,132; semipermeable polystyrene derivatives; semipermeable (polysodiumstyrenesulfonate); semipermeable poly(vinylbenzyltrimethyl) ammonium chloride; semipermeable polymer exhibiting a fluid permeability of $10^{-1}$ to $10^{-10}$ (cc.mil/cm$^2$ hr.atm) expressed as per atmosphere or hydrostatic or osmotic pressure difference across a semipermeable wall. The polymers are known to the art in U.S. Pat. Nos. 3,845,770; 3,916,899 and 4,160,020, and in *Handbook of Common Polymers*, by Scott, J. R. and Roff, W. J., 1971, published by CRC Press, Cleveland, Ohio.

The microporous materials used for forming exit means 13 or microporous wall 24 generally can be described as having a sponge-like appearance that provides a supporting structure for interconnected pores or voids. The material can be isotropic wherein the structure is homogeneous throughout a cross-sectional area, the material can be anisotropic wherein the structure is nonhomogeneous throughout a cross-sectional area, or the materials can have both cross-sectional areas. The microporous materials can be opened celled, wherein the pores are continuous, or connected pores having an opening on both faces of microporous wall 19. The micropores are interconnected through tortuous paths of regular and irregular shapes including curved, linear, curved-linear, randomly oriented continuous pores, hindered connected pores, and other interconnected porous paths discernible by microscopic examination.

Generally the microporous materials are characterized as having a reduced bulk density as compared to the bulk density of the corresponding non-porous precursor microporous material. The morphological structure of the total microporous material will have a greater proportion of total surface area than the non-porous material. The microporous material can be further characterized by the pore size, the number of pores, the tortuosity of the microporous paths, and the porosity which relates to the size and the number of pores. The pore size of a microporous material is easily ascertained by measuring the observed pore diameter at the surface of the material under the electron microscope. Generally materials possessing from 5% to 95% pores, and having a pore size of from 10 angstroms to 100 microns can be used for making wall means 13 and 14. Relationships of the above type are discussed in *Transport Phenomena In Membranes*, by Lakshminatayania, N., Chapter 6, 1969, published by Academic Press, Inc., New York. Microporous materials are described in *Science*, Vol. 170, pp 1302-1305, 1970; *Nature*, Vol. 214, p 285, 1967; *Polymer Engineering and Science*, Vol. 11, pp 284-388, 1971; U.S. Pat. Nos. 3,567,809 and 3,751,537; in *Industrial Processing With Membranes*, by Lacey, R. E., and Loeb, Sidney, pp 131-134, 1972, published by Wiley Interscience, New York.

Microporous materials are commercially available and they can be made by art known methods. The microporous materials can be made by etched nuclear tracking; by cooling a solution of a flowable polymer below the freezing point whereby the solvent evaporates from the solution in the form of crystals dispersed in the polymer, and then curing the polymer followed by removing the solvent crystals; by cold stretching or hot stretching at low or high temperatures until pores are formed; by leaching from a polymer a soluble component by an appropriate solvent; by ion exchange reaction, and by polyelectrolyte processes. In a presently preferred embodiment the microporous means or wall is formed in the environment of use from a precursor polymicroporous means or wall forming material. This latter material contains a pore former that is removed from the precursor by eroding, dissolving or leaching a pore former therefrom, thus forming an operable microporous means or wall. The pore formers useful for the present purpose are a member selected from the group consisting of about 1 to 50%, or more, by weight of a solid pore former, about 0.5 to 20%, percent by weight, of a liquid pore former, and mixtures thereof. In another embodiment the microporous means and/or wall can be formed by a compression coating technique. In this latter embodiment a rigid microporous material, substantially free of substances soluble or swellable in the fluid present in the environment of use, can be formed by compression coating a microporous material around the compartment forming ingredients. Generally a microporous means and/or wall is formed under a compression pressure of 500 to 5000 kg/cm$^2$, usually in a rotary machine. Processes for preparing microporous means and walls are described in *Synthetic Polymer Membranes*, by R. E. Kesting, Chapters 4 & 5, 1971, published by McGrawHill, Inc.; *Chemical Reviews, Ultrafilter Membranes and Ultrafiltration*, Vol. 18, pp 373-455, 1934., *Polymer Engineering and Science*, Vol. 11, pp 284-288, 1971 *J. Appln. Poly. Sci.*, Vol. 15, pp 811-829, 1971; in U.S. Pat. Nos. 3,565,259; 3,615,024; 3,751,536; 3,801,692; 3,852,224; 3,849,528 and 3,929,509; and in Great Britain Pat. No. 1,459,356.

Materials suitable for forming a microporous means and/or wall include polycarbonates comprising linear polyesters of carbonic acid in which carbonate groups recur in polymer chains by phosgenation of a dihydroxy aromatic such as a bisphenol; microporous poly(vinyl chloride); microporus polyamides such as polyhexamethylene adipamide; microporous modacrylic copolymers including those formed of polyvinyl and acrylonitrile; styrene-acrylic acid copolymers; microporous polysulfones characterized by diphenylene sulfone groups in the linear chain thereof; halogenated polymers such as polyvinylidene fluoride, polyvinylfluoride and polyfluorohalocarbon; polychloroethers; cellulose esters, cellulose ethers, cellulose acylates; acetal polymers such a polyformaldehyde, polyesters prepared by esterification of a dicarboxylic acid or anhydride with a polyol; poly(alkylenesulfides); phenols; polyesters; microporous poly(saccharides) having substituted and unsubstituted anhydroglucose units; asymetric porous polymers; cross linked olefin polymers; hydrophobic and hydrophilic microporous homopolymers, copolymers or interpolymers having a reduce bulk density, and the materials described in U.S. Pat. Nos.* 3,595,752; 3,643,178., 3,654,066., 3,709,774; 3,718,532; 3,803,061; 3,852,224; 3,852,388; 3,853,631, and 3,948,254., and in Great Britain Pat. No. 1,126,849., and in Chem. Absts., Vol. 71, 4274F, 22572F and 22573F, 1969.

Additional microporous materials include materials that are substantially insoluble in the fluid present in the environment of use, are inert, non-disintegrating, non-eroding and are materials that can be compressed in powder form, applied by air suspension, dipping techniques, and the like. Exemplary materials include poly(urethanes); copolymers of divinyl chloride and acrylonitrile; organic materials such as cross linked, chain extended poly(urethanes); microporous poly(urethanes) in U.S. Pat. No. 3,524,753., poly(imides); poly(benzimidazoles); collodion(cellulose nitrate with 11% nitrogen); regenerated proteins; microporous materials prepared by diffusion of a multivalent cations into polyelectrolyte sols as in U.S. Pat. No. 3,565,259; anisotropic microporous materials of ionically associated polyelectrolytes; microporous polymers formed by the coprecipitation of a polycation and a polyanion as described in U.S. Pat. Nos. 3,276,589; 3,541,006; and 3,546,142; derivatives of poly(styrene) such as poly(sodium styrene sulfone) and poly(vinylbenzyltrimethylammonium chloride); the microporous materials disclosed in U.S. Pat. Nos. 3,615,024; 3,646,178, and 3,852,224; the microporous materials having a plurality of micropores as disclosed in U.S. Pat. No. 3,948,254, and the like.

The expression, "pore former" includes pore forming solids and pore forming liquids. The later expression, that is, the term, "liquid", generically embraces semisolids, pastes and viscous fluids. The pore formers can be inorganic or organic. The term, "pore former", for both solids and liquids, includes substances that can be dissolved, eroded, extracted or leached from the precursor microporous means or wall by fluid present in the environment of use to form an operable, open celled type microporous means or wall. Additionally, the pore formers suitable for the invention include pore formers that can be dissolved, leached, eroded or extracted without causing physical or chemical changes in the polymer. The pore forming solids can have a size of about 0.1 to 200 microns and they include alkalimetals salts such as lithium chloride, lithium carbonate, sodium chloride, sodium bromide, sodium carbonate, potassium chloride, potassium sulfate, potassium phosphate, sodium benzoate, sodium acetate, sodium citrate, potassium nitrate, and the like. The alkaline earth metal salts such as calcium phosphate, calcium nitrate, calcium chloride, and the like. The transition metal salts such as ferric chloride, ferrous sulfate, zinc sulfate, cupric chloride, manganese fluoride, manganese fluorosilicate, and the like. Organic compounds such as polysaccharides including sucrose, glucose, fructose, mannitol, mannose, galactose, addohexos, altrose, talose, sorbitol, and the like. Organic aliphatic ols including diols, polyols; organic ols including diols and polyols, and other polyols such as polyhydric alcohol, polyalkylene glycol, polyglycol, poly (α-ω)-alkylenediols, and the like. The pore formers are non-toxic and on their removal from the means or wall channels formed through the means or wall that fills with fluid. The channels become, in one embodiment, means or paths for releasing a beneficial agent from the delivery device. The pores extend from the inside means or wall to the outside thereof for effective release of beneficial agent 17 to the exterior of the delivery system 10. In a presently preferred embodiment, the means or wall comprises 1 to 50% of pore former based on the weight of the polymer of a pore forming agent selected from the group consisting of inorganic salts, organic salts, carbohydrates and ols are used when the pores are formed during use in a biological environment.

Materials useful for forming internal wall 14 are materials used for forming a capsule. Capsule wall member 14 generally comprises a single piece, or a two piece, construction and, in a presently preferred embodiment, it is tubular shaped and it has a mouth at one end, and at the end distant therefrom it is closed in a hemispherical or dome shaped end. The capsule member serves as a hollow body having a wall that surrounds and defines an interior compartment provided with an opening for establishing communication with the exterior of the capsule and for filling the capsule. In one embodiment a capsule is made by dipping a mandrel, such as a stainless steel mandrel, into a bath containing a solution of a capsule wall forming material to coat the mandrel with the material. Then, the mandrel is withdrawn, cooled, and dried in a current of air. The capsule is stripped from the mandrel and trimmed to yield a capsule with an internal lumen. Materials used for forming capsules are the commercially available materials including gelatin, gelatin having a viscosity of 15 to 30 millipoises and a bloom strength up to 150 grams; gelatin having a bloom value of 160 to 250; a composition comprising gelatin, glycerine water and titanium dioxide; a composition comprising gelatin, erythrosin, iron oxide and titanium dioxide, a composition comprising gelatin, glycerine, sorbitol, potassium sorbate and titanium dioxide; a composition comprising gelatin, acacia, glycerin and water; water soluble polymers that permit the transport of water therethrough and can be made into capsules, and the like.

Expandable means 18 housed in compartment 15 generically comprises, in a presently preferred embodiment, a hydrogel composition. The hydrogel composition can be noncross-linked, or it is, optionally, cross-linked, and it possesses properties, such as the ability to absorb and/or imbibe an exterior fluid through a semipermeable component of the wall. Hydrogels possessing osmotic properties exhibit an osmotic pressure gradient across said semipermeable wall 12 against a fluid outside of delivery system 10. The materials used for forming the expandable, swellable hydrogel means are polymeric materials neat, and polymeric materials blended with an osmotic agent. These materials in either instant, interact with water or a biological aqueous fluid, absorb and/or imbibe fluid and swell or expand to an equilibrium state. The polymer exhibits the ability to retain a significant fraction of the fluid in the polymer molecular structure. The polymers presently preferred are gels, that is, polymers that can swell or expand to a very high degree, usually exhibiting a 2 to 50 fold volume increase. Hydrophilic polymers that imbibe fluid, swell and expand are known also as osmopolymers. The osmopolymers, like other hydrophilic polymers, can be noncross-linked or lightly cross-linked. The cross-links can be covalent or ionic bonds with the polymer possessing the ability to swell in the presence of fluids. The hydrophilic polymers, when cross-linked with nonhydrolyzable bond, will not dissolve in the fluid, but will swell and expand in the presence thereof. The polymers can be of plant, animal or synthetic origin. Polymeric materials useful for the present purpose include poly(-hydroxyalkyl methacrylate) having a molecular weight of from 5,000 to 5,000,000; poly(vinylpyrrolidone) having a molecular weight of from 10,000 to 360,000; anionic and cationic hydrogels; poly(electrolyte) complexes; poly(vinyl alcohol) having a low acetate residual; a swellable mixture of agar and carboxymethyl cellulose; a swellable composition comprising methyl cellulose mixed with a sparingly cross-linked agar; a water-swellable copolymer produced by a dispersion of finely divided copolymer of maleic anhydride with styrene, ethylene, propylene, or isobutylene; water swellable polymer of N-vinyl lactams; and the like.

Other fluid absorbing and/or imbibing and fluid retaining polymers useful for forming the hydrophilic, expandable push member include pectin having a molecular weight ranging from 30,000 to 300,000; polysaccharides such as agar, acacia, karaya, tragacanth, algins and guar; Carbopol® acidic carboxy polymer and its salt derivatives; polyacrylamides; water-swellable indene maleic anhydride polymers; Good-rite® polyacrylic acid having a molecular weight of 80,000 to 200,000; Polyox® polyethylene oxide polymers having a molecular weight of 100,000 to 5,000,000; starch graft copolymers; Aqua-Keep® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000, and the like. In a preferred embodiment, the expandable member is formed from polymers and polymeric compositions that are thermoformable. Representative polymers possessing hydrophilic properties are known in U.S. Pat. Nos. 3,865,108; 4,002,173; 4,207,893; 4,327,725, and in *Handbook of Common Polymers*, by Scott and Roff, published by Cleveland Rubber Company, Cleveland, Ohio.

The swellable, expandable polymer, in addition to providing a driving source for delivering beneficial agent 17 from dispenser 10, further serves to function as a supporting matrix for an osmotically effective solute. The osmotic solute can be homogeneously or heterogeneously blended with the polymer to yield the desirable expandable member 18. The composition in a presently preferred embodiment comprises at least one polymer and at least one osmotic solute blended together. Generally, a composition will comprise about 20% to 90% by weight of polymer and 80% to 10% by weight of osmotic solute, with a presently preferred composition comprising 35% to 75% by weight of polymer and 65% to 25% by weight of osmotic solute.

The osmotically effective compound that can be blended homogeneously or heterogeneously with the swellable polymer to form a push or driving member are the osmotically effective solutes that are soluble in fluid imbibed across a semipermeable wall and into the swellable polymer. The osmotically effective compounds exhibit an osmotic pressure gradient across a semipermeable wall against an external fluid. Osmotically effective compounds are known also as osmotically effective solutes and also as osmagents. Osmotically effective osmagents useful for the present purpose include magnesium sulfate, magnesium chloride, sodium chloride, lithium chloride, potassium chloride, potassium sulfate, sodium sulfate, mannitol, urea, sorbitol, inositol, succrose, glucose, and the like. The osmotic pressure in atmospheres, ATM, of the osmagents suitable for the invention will be greater than zero ATM, generally from eight ATM up to 500 ATM, or higher. Standard procedures for measuring osmotic pressure are known in U.S. Pat. Nos. 4,331,728 and 4,519,801.

The thermo-responsive composition 16, containing beneficial agent 17 homogeneously or heterogeneously dispersed or dissolved therein, is formed in a presently preferred embodiment of a heat sensitive, hydrophilic or hydrophobic material that exhibits storage and solid-like properties at room temperature of up to 24° C., and within a few centigrade degrees thereof, and exhibits a dispensing range of 25° C. to 45° C., and, in a preferred embodiment, a dispensable point that approximates mammalian body temperatures of 37° C. to 45° C., and within a few centigrade degrees thereof. The present invention uses the phrases "melting point", "melting range", "softening point", "pour point" or "liquifies", to indicate the temperature at which the thermo-responsive composition melts, undergoes dissolution, or forms a paste-like ribbon, or dissolves, as it takes up thermal energy or heat, to form a dispensable carrier 16 so it can be used for dispensing beneficial agent 17 from dispenser 10.

The term, "thermo-responsive" as used for the purpose of this invention embraces thermoplastic compositions comprising means for containing a beneficial agent and for forming a dispensable carrier in a biological environment of use. The thermoplastic composition exhibits means for softening or becoming dispensable in response to heat and solidifying or thickening again when cooled. The term also includes thermotropic compositions capable of undergoing change in response to the application of energy in a gradient manner; these are temperature sensitive compositions in their response to the application or withdrawl of thermal energy. The term, "thermo-responsive" as used for the purpose of this invention in a preferred embodiment denotes the physical-chemical property of a composition agent carrier to exhibit solid, or solid-like properties at temperatures up to 24° C., and become fluid, semisolid or viscous when contacted by heat temperatures from 25° C., usually in the range of 25° C. to 45° C. The thermoresponsive carrier is heat sensitive and preferably originally anhydrous and it has the property of melting, dissolving, undergoing dissolution, softening, or liquifying at the rising and elevated temperatures, thereby making it possible for the dispenser 10 to deliver the thermo-responsive carrier 16 with the beneficial agent 17 homogeneously or heterogeneously blended therein. The thermo-responsive carrier generally is lipophilic and hydrophobic, but does not exclude water miscible and hydrophilic carriers. Another important property of the carrier 16 is its ability to maintain the stability of agent 17 contained therein during storage and during delivery of agent 17. Exemplary of thermoplastic compositions include a member selected from the group consisting of monoglyceride, diglyceride, triglyceride, monoglyceride of a fatty acid, diglyceride of a fatty acid, triglyceride of a fatty acid, glycerides with emulsifier, eutetic mixture of mono-, di- and triglycerides, ethoxylated glycerides, partially hydrogenated plant, vegetable and animal fats, hydrogenated plant, vegetable and animal fats, alklylene glycol fatty and esters, polyalkylene glycol fatty acid esters, triglycerides of fatty acids having 12 to 18 carbons, triglycerides of vegetable fatty acids with monoglycerides, triglycerides of vegetable fatty acid with diglycerides, petroleum-based food grade waxes, and the like. The thermoplastic composition is nontoxic and nonirritating to animal tissues, compatible with a broad range of active agents, is stable on storage, exhibits a beneficial agent release pattern, and can be used in hand or machine manufacturing procedures.

Representative thermo-responsive compositions and their melting points are as follows: cocoa butter, 32°-34° C; cocoa butter plus 2% beeswax, 35°-37° C.; propylene glycol monostearate and distearate, 32°-35° C.; hydrogenated oils such as hydrogenated vegetable oil, 36°-37.5° C; 80% hydrogenated vegetable oil and 20% sorbitan monopalmitate, 39°-39.5° C.; 80% hydrogenated vegetable oil and 20% polysorbate 60, 36°-37° C.; 77.5% hydrogenated vegetable oil, 20% sorbitan trioleate and 2.5% beeswax, 35°-36° C.; 72.5% hydrogenated vegetable oil, 20% sorbitan trioleate, 2.5% beeswax and 5.0% distilled water, 37°-38° C.; mono-, di-, and triglycerides of acids having from 8-22 carbon atoms including saturated and unsaturated acids such as palmitic, stearic, oleic, lineolic, linolenic and archidonic; glycerides of fatty acids having a melting point of at least 32° C. such as monoglycerides, diglycerides and triglycerides of vegetable fatty acids having 10 to 18 carbon atoms obtained from coconut oil, olive oil and the like; partially hydrogenated cottonseed oil 35°-39° C.; hardened fatty alcohols and fats, 33°-36° C.; hexadienol and anhydrous lanolin thiethanolamine flyceryl monostearate, 38° C.; eutectic mixtures of mono-, di-, and triglycerides, 35°-39° C.; Witepsol ® #15, triglyceride of saturated vegetable fatty acid with monoglycerides, 33.5°-35.5° C.; Witepsol ® H32 free of hydroxyl groups, 31°-33° C.; Witepsol ® W25 having a saponification value of 225-240 and a melting point of 33.5°-35.5° C.; Witepsol ® E75 having a saponification value of 220-230 and a melting point of 37°-39° C.; a polyalkylene glycol such as polyethylene glycol 1000, a linear polymer of ethylene oxide, 38°-41° C.; polyethylene glycol 1500, melting at 38°-41° C.; polyethylene glycol monostearate, 39°-42.5° C.; 33% polyethylene glycol 1500, 47% polyethylene glycol 6000 and 20% distilled water, 39°-41° C.; 30% polyethylene glycol 1500, 40% polyethylene glycol 4000 and 30% polyethylene glycol 400, 33°-38° C.; mixture of mono-, di-, and triglycerides of saturated fatty acids having 11 to 17 carbon atoms, 33°-35° C.; block polymer of 1,2-butylene oxide and ethylene oxide; block polymer of propylene oxide and ethylene oxide; block polymer of polyoxyalkylene and propylene glycol, food grade wax composition that soften continuously in the presence of heat, and the like. The thermo-responsive composition is a means for storing a beneficial agent as a storagable composition at a temperature of up to 24° C. for maintaining an immiscible boundary at the thermo-responsive, swelling interface, and for dispensing the agent in a flowable composition at a temperature greater than 25° C., and preferably in the range of 25° to 45° C. The thermo-responsive composition on being dispensed into a biological environment are easily excreted, metabolized, assimilated, or the like, for effective use of the beneficial agent.

Representative material for forming the first lamina means 19 for maintaining the separate identity of thermo-responsive composition 16 containing agent 17 and expandable member 18 denotes a composition that possesses film-forming properties, preferably is soft, flexible and adapts to the configuration of the internal surface of dispenser 10. In a presently preferred embodiment lamina 19 is a wax. The term as was used herein generically denotes a petroleum based food-grade wax or an ester of a high molecular weight fatty acid with a high molecular weight alcohol. Materials useful for this purpose include waxes, which are a different wax composition than a wax comprising the thermo-responsive composition; for example, the former can be a higher melting point wax. The waxes acceptable for this present purpose exhibit a melting point or a solidification point of about 45° C. to 110° C. and they are selected from the group consisting of mineral, vegetable, plant, animal petroleum, and synthetic waxes. Representative waxes include a member selected from the group including the following wax and its melting range: montan wax, 80°–90° C.; ozokerite wax, 55°–110° C., usually 70° C.; carnuba wax, 84°–86° C.; myricyl cerotate wax, 85° C.; beeswax, 63° C.; spermaceti, 45° C.; ceresine, 48° C.; gama wax, 47° C.; Japan wax, 63° C.; ouricury, 83° C.; ceresin wax, 68°–72° C.; castor wax, 85° C.; Witco wax, 72° C.; and the like. Additionally, reinforcing agents such as Cabosil can be incorporated into the wax for improving structural integrity.

Representative materials for forming lamina 22 for conveying the expanding force of expandable polymer 18 against thermo-responsive composition 16 containing beneficial agent 17 include film-forming polymer that are capable of receiving and transmitting an applied force, such as olefin polymers, vinyl polymers, synthetic condensation polymers, natural polymers and organosilicon polymers. Representative of specific polymers include polyethylene, polypropylene, polytetrafluoroethylene, polystyrene, polyvinyl acetate, polyvinyl formal, cross-linked polyvinyl acetate, polyvinyl butyral, polyacrylate, polymethyacrylate, polyvinyl chloride, cellulose acetate, polyamides, polyester, rubber, styrene butadiene rubber, polyurethane, polysilicone, and the like. The lamina can have a thickness from 1 mil to 15 mm, or more, for effectively transmitting the in vivo generated force.

The expression, "beneficial agent" as used herein denotes any beneficial agent 17 or compound that can be delivered by device 10 to produce a beneficial and useful result. The beneficial agent can be from insoluble to very soluble in the heat sensitive carrier means 16. The term, "beneficial agent" includes biocide, parasiticide, fungicide, larvicide, flukicide, medicine or drug, nutrient, vitamin, food supplement, mineral, anthelmintic, anti-infestation, growth promotant, ionophores, and other agents that benefit the environment of use.

In the specification and the accompanying claims the term, "beneficial agent" includes any physiologically or pharmacologically active substances that produce a local or systemic effect in animals, including warm-blooded mammals; humans and primates; household, sport, farm and zoo animals. The term, "physiologically" as used herein denotes the administration of a drug to produce normal levels and functions. The term, "pharmacologically" denotes variations in response to an amount of drug administered to the host. *Stedman's Medical Dictionary*, 1966, published by Williams and Wilkins, Baltimore, Md. The beneficially active drugs 17 that can be delivered by device 10 include inorganic and organic drugs, such as drugs that act on the central nervous system, depressants, hypnotics, sedatives, psychic energizers, tranquilizers, anticonvulsants, muscle relaxants, antiparkinson agents, analgesic, anti-inflamatory, anesthetics, muscle contractants, antimicrobials, antimalarials, hormonal agents, contraceptives, diuretics, sympathomimetics, antiparasitics, neoplastics, hypoglycemics, opthalmics, electrolytes, cardiovascular drugs and the like.

Exemplary drugs that can be delivered by the delivery device are prochlorperazine edisylate, ferrous sulfate, animocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridehexethyl chloride, phenformin hydrochloride, methylphenidate hydrochloride, oxprenolol hydrochloride, metroprolol tartrate, cimetidine hydrochloride, diphenidol, meclizine hydrochloride, prochlorperazine maleate, phenoxybenzamine, thiethylperazine maleate, anisindone, diphenadione, erythrityl tetranitrate, dizoxin, isofurophate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, esterogenic steroids, progestational steriods, corticosteroids, hydrocortisone, 17 β-estradiol, ethenyl estradiol, ethinyl estradiol 3-methyl ester, prednisolong, hydrocorticosterone acetate, triamcinolone, methyltesterone, 17 β-hydroxyprogesterone acetate, 19-nor-progesterone, norgestrel, norethindone, norethiderone, progesterone, norgesterone, norethynodrel, and the like.

Examples of other beneficial drugs that can be delivered by the delivery device include aspirin, indomethacin, naproxen, fenoprofen, sulindac, diclofenac, indoprofen, nitroglycerin, propanolol, valproate, timolol, atenolol, alprenolol, cimetidine, clonidine, imipramine, levodopa, chloropromazine, reserpine, methyl-dopa, dihyroxyphenylalanine, prvaloxyloxyethyl ester of α-methyldopa hydrochloride, theophylline, calcium gluconate, ferrous lactate, vincamine, diazepam, phenoxybenzamine, blocking agents, and the like. The beneficial drugs are known to the art in *Pharmaceutical Sciences*, by Remington, 14th Ed; 1979, published by Mack Publishing Co; Easton, Pa.; *The Drug, The Nurse, The Patient, Including Current Drug Handbook*, 1974–1976, by Falconer et al, published by Sunder Co; Philadelphia, Pa, and *Medical Chemistry*, 3rd Ed; Vol. 1 & 2, by Burger, published by Wiley-Interscience, New York.

Representative of beneficial medicaments that can be delivered to warm-blooded animals, exemplified by ruminants, using the delivery system of this invention, include anthelmintics such as mebendazole, levamisole, albendazole, cambendazole, fenbendazole, parbendazole, oxfendazole, oxybendazole, thiabendazole, tichlorfon, praziquantel, morantel and parantel, and the like; antiparasitic agents such as avermectin and ivermectin, as disclosed in U.S. Pat. Nos. 4,199,569 and 4,389,397, both assigned to Merck & Co; and in *Science,* Vol. 221, pp 823-828, 1983, wherein said ivermectin antiparasitic drugs are disclosed as useful for aiding in controlling commonly occurring infestations in animals, such as roundworms, lung worms, and the like, and said ivermectin also being useful for the management of insect infestations such as grub, lice, mange mite, and the like; antimicrobial agents such as chlortetracycline, oxytetracycline, tetracycline, streptomycin, gentamicin, dihydrostreptomycin, bacitracins, erthromycin, ampicillins, penicillins, cephalosporins, and the like; sulfa drugs such as sulfamethazine, sulfathiazole, and the like; growth stimulants such as Monesin ® sodium and Elfazepam ®; defleaing agents such as dexamethazone and flumethazone; rumen fermentation manipulators and ionophores such as lasalocid, virginiamycin, salinomycin and ronnel; minerals and mineral salts; anti-bloat agents such as organopoly siloxanes; hormone growth supplements such as stilbestrol; vitamines; antienteritis agents such as furazolidone; growth efficiency factors such as $\beta$-agonists, elenbuterol, nutritional supplements such as lysine monohydrochloride, methionine, magnesium carbonate, ferrous and ferric compounds, copper oxide, cobalt sulphate, sodium selenite, potassium iodide, zinc oxide and managese sulphate, and the like, and chemical markers such as chromic oxide, salts of ytterbium and erbium.

The agents or drugs can be in various forms, such as uncharged molecules, molecular complexes, pharmacologically acceptable salts such as hydrochlorides, hydro-bromide, sulfate, laurylate, palmitate, phosphate, nitrate, borate, acetate, maleate, tartrate, oleate, salicylate, and the like. For acid drugs, salts of metals, amines, or organic cations, for example, quaternary ammonium can be used. Derivatives of drugs such as esters, ethers, amides, and the like, can be used. Also, an agent or a drug that is lipid insoluble can be used neat or in a form that is a lipid soluble derivative thereof, and on its release from the device can be converted by body activities to biologically active forms. Drug that are water insoluble can be in form that is converted by enzymes, hydrolyzed by body pH or other metabolic processes, to the original biologically active form. The amount of drug present in a device is initially in a present embodiment, an amount in excess of the amount that can be dissolved in the heat sensitive formulation. Generally, the device can contain from 0.05 ng to 5 g or more, with individual devices containing, for example, 25 ng, 1 mg, 5 mg, 125 mg, 250 mg, 500 mg, 750 mg, 1.5 g, 10 g, 25 g, 50 g, and the like. The device can dispense from 0.1 to 1500 mg/hr. For example, for avermectins such as ivermectin the device can be dispensed over a dispensing range of 1 mg/day to 50 mg/day and the like. The devices can dispense agent from 1 day to 6 months or more.

The term, "animal" as used herein generically denotes an animal and its normal average temperature in centigrade, usually measured rectally, as follows: man, 37° C.; camel, 37°-38° C.; cattle, 38°-39° C.; dog, 38°-39° C.; goat, 38°-39° C.; sheep, 39°-40° C.; swine, 37°-38° C.; deer, 38°-39° C.; bison, 39° C.; giraffe, 37°-38° C.; horse, 38° C, and elephant, 36°37° C.

The expression, "means for releasing a beneficial agent" as used herein includes at least one preformed passageway, or at least one passageway formed when the device is in use. The passageway in either embodiment will pass through the wall for communicating with the compartment for releasing the beneficial agent from the device. The expression, "means for releasing beneficial agent" includes passageway, aperture, bore, pore, porous element through which the beneficial agent can migrate, hollow fiber, capillary tube, microporous member, and the like. The means for releasing agent include a material that is removed from the wall during use such as eroding in the environment of use to produce at least one passageway in the device. Representative materials suitable for forming a passageway include erodible poly(glycolic), poly(lactic) in the wall, gelatinous filaments, poly(vinyl alcohol), and the like. The passageway can be formed by leaching a material such as sorbitol from the wall. The passageway can have any shape such as round, triangular, square, elliptical, irregular, and the like. The device can be constructed with more than one passageway, especially for dispensing released agent over a wide area. In a preferred embodiment, when the device is fabricated with more than one passageway, they can be constructed as the functional equivalent of a single passageway. The passageway can be formed also by mechanical drilling or laser drilling through the wall. A description of means for releasing a beneficial agent as described herein is disclosed in U.S. Pat. Nos. 3,845,770 and 3,906,899. Procedures for forming at least one passageway of governed porosity by leachnng from a wall, such as a cellulose wall, a pore former is disclosed in U.S. Pat. Nos. 4,200,098; 4,235,236; 4,309,996, and 4,320,759. The leaching or dissolving of a pore former from a wall forming material is known also in U.S. Pat. Nos. 4,256,108; 4,265,874 and 4,344,929. Laser drilling equipment having photo detection means for orienting a device for selecting a surface for drilling a passageway for communicating with a preselected area inside a device is known in U.S. Pat. Nos. 4,063,064 and 4,008,864.

The wall, including the semipermeable wall, the microporous wall and the laminated wall can be formed by molding, air spraying, dipping or brushing with a wall forming composition. Other and presently preferred techniques that can be used for applying wall forming materials are the air suspension procedure and the pan coating procedure. The air procedure consists is suspending and tumbling the compartment forming materials in a current of air and a wall forming composition until the wall surrounds and coats the materials. The procedure can be repeated with a different wall forming composition to form a laminated wall. The air suspension procedure is described in U.S. Pat. No. 2,799,241; *J. Am. Pharm. Assoc;* Vol. 48, pp 451 to 459; and ibid, Vol. 49, pp 82 to 84, 1960. Other standard manufacturing procedures are described in *Modern Plastics Encyclopedia,* Vol. 46, pages 62 to 70, 1969; and in *Pharmaceutical Sciences,* by Remington, 14th Ed; pp 1626 to 1678, 1970, published by Mack Publishing Co; Easton, Pa.

Exemplary solvents suitable for manufacturing the walls include inert inorganic and organic solvents that do not adversely harm the materials, the wall, the beneficial agent, the thermo-responsive composition, the expandable member, and the final dispenser. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl alcohol, n-gutyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naptha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Generally, for the present purpose the wall is applied at a temperature a few degrees less than the melting point of the thermo-responsive composition. Or, the thermoplastic composition can be loaded into the dispenser after applying the wall.

DESCRIPTION OF EXAMPLES OF THE INVENTION

The following examples are merely illustrative of the present invention and they should not be construed as limiting the scope of the invention in any way, as these examples and other equivalents thereof will become more apparent to those skilled in the art in the light of the present disclosure, the drawings and the accompanying claims.

EXAMPLE 1

A dispensing system manufactured in the shape of a dispenser for the controlled delivery of ivermectin is made as follows: First, 193 g of Butronic ® L-1 polyol, a block polymer formed by the polymerization of 1,2-butylene oxide to which ethylene oxide, is added, as reported in *Cosmetics and Toiletries,* Vol. 97, pp 61–66, 1982, which polymer flow at a pour point of 39° C., is melted at 55° C., and then 13.98 g of ivermectin is added thereto using a high sheer ultrasonic mixer. The resulting mixture is placed in a vacuum oven at 55° C. and the pressure reduced to less than 10 mm of mercury. The ivermectin Butronic ® composition is allowed to remain in the vacuum for a period of about 10 minutes, for removing entrapped air. Next, 4 g of the resulting thermoplastic drug formulation is poured into a gelatin capsule that is previously charged with a 33 g stainless steel density member having a bore therethrough. Then, 2 g of beeswax, melted at 63° C., is charged onto the thermoplastic composition to form a contacting lamina. The wax is substantially impermeable to the passage of water for substantially restricting any extraction of the active agent by an aqueous type fluid that is absorbed into the dispenser by the expandable polymer. Then, an expandable driving member comprising 2.1 g of sodium chloride and 4.9 g of the sodium salt of polyacrylic acid available as Carbopol ® 934P is compressed into a tablet. The tablet is formed using a 18.2 mm tableting tool and 3½ tons of compression force. The tablet has a final shape that corresponds to the internal shape of the opening of the capsule. The tablet member then is inserted into the opened end of the capsule until contact is made with the drug polyol formation. Next, the capsule is coated in a pan coater with a rate controlling wall comprising 1.8 g of 91% cellulose acetate butyrate and 9% polyethylene glycol 400. The wall is coated from a 5% wt/wt solution in methylene chloride methanol 90:10 v/v solvent system. The wall coated delivery systems then are dried at 30° C. for 24 hours. Next, a 30 mil exit passageway is drilled through the semipermeable wall using a high speed mechanical drill for communicating the passageway with the bore. The passageway bore arrangement established communication with the heat-responsive drug formulation for delivering it from the delivery system. The dispenser made according to this example has an average release rate of 0.6 mg per hour over a 480 hr period of time.

EXAMPLE 2

A delivery system is made according to the procedure set forth in Example 1, with the conditions as set forth, except that in this example the heat-responsive composition comprises 46.6 g of ivermectin and 200 g of polyethylene glycol 400 distearate, the intermediate lamina comprises ouricury wax that is added in a lamina forming amount at a temperature of about 82° to 84° C., and the expandable-swellable composition comprises 70% by weight of poly(ethylene oxide) having a molecular weight of 3,000,000 and 30% by weight of sodium chloride.

EXAMPLE 3

A dispensing system is prepared for manufacturing a dispenser according to the procedure of Example 1, with the conditions as previously set forth, except that in this example the thermo-responsive composition comprises a food grade Witco multiwax that is soft at a temperature of 35° C. and softens in the presence of rising temperatures from 35° C. to 40° C. and can be dispensed from the dispensing system under a hydrostatic pressure of 8 to 12 psi.

EXAMPLE 4

A dispenser is prepared as follows: First, the body section of a capsule is positioned with its mouth in an upright position, and a dense stainless steel element inserted into the hemispherical end of the capsule. The density element is machined and its shape matches the internal shape of the capsule. Next, a layer of an expandable-swellable composition is charged on top of the density element. The composition comprises 25% by weight of sodium chloride and 75% by weight of poly-(ethylene oxide) having a molecular weight of 200,000. The expandable forming ingredients are blended in a commercial blender with heat for 20 minutes to yield a homogeneous composition. The heat composition is charged into the capsule forming a layer that occupies about ⅓ of the capsule. Next, a lamina comprising polyethylene and stamped-cut to have a shape that corresponds to the internal shape of the capsule is placed against the expandable layer in contacting arrangement. Then, a lamina comprising 2 g of melted beeswax is charged into the capsule in laminar arrangement with the previously positioned lamina, and the manufacture allowed to cool to room temperature, about 22° C. Next, a heat-sensitive drug formulation comprising an eutetic"mixture of 77% neutral fat having a melting point of 35°37° C. and 19.5% paraffin having a melting point of 52° C. is heated and 3.5% levamisole is added thereto. Then, the heated mixture is cooled to about 40° C. and injected into the capsule in contacting relation with the expandable layer, and the capsule allowed to cool to room temperature.

Then, a solution of cellulose acetate, 15 wt percent, with an acetyl content of 39.8%, is prepared in a methylene chloride-methanol solvent system and the capsule coated with a semipermeable wall. The wall is applied by dipping it into the coating solution 15 times, first for a 5 second dip, then for two 10 second dips, then for a 30 second dip and then for 1 minute per dip, with an intervening 5 minute drying period. Following the dipping the delivery dispenser is dried at room temperature, 72° F., about 22° C., for 5 days. The procedure applies about a 2 mm thick semipermeable wall. A passageway is laser drilled through the semipermeable wall connecting the exterior of the dispenser with the heat sensitive drug formulation for releasing it at a controlled rate over time.

EXAMPLE 5

A dispensing system for delivering beneficial nutrients to warm-blooded ruminants is prepared as follows: First, a mold having a shape and configuration corresponding to the internal diameter and the hemispherical closed end of a wide-mouth capsule is filled with an expandable forming composition comprising 30 parts of ethyleneglycol monomethacrylate containing 0.12 parts of ethyleneglycol dimethacrylate and 10 parts of a 0.13% aqueous solution of sodium disulfate in aqueous ethanol. The composition polymerizes at 30° C., and after 20 minutes following equilibrium to room temperature, the solid layer is removed from the mold. The solid expandable layer then is inserted through the mouth of the capsule into the hemispherical area of the capsule. Then, a lamina of paraffin wax having a melting point of about 52° C. is added to the subassembly and, after cooling, a dense member made of stainless steel machined in the shape of a tablet is placed inside the capsule in contacting laminar arrangement with the expandable layer. Next, the remainder of the capsule is filled with a melted composition comprising 2.5% L-lysine HCl, 1.5% DL-methionine, 21% glycergelatin and 75% theobromo oil, a glyceride of stearic acid, palmitic acid and lauric acid, to form, on cooling to room temperature, the thermo-responsive composition in laminar position with the dense member. Next, the filled capsule is coated with a surrounding wall comprising cellulose acetate containing 10% polyethylene glycol 400. The semipermeable wall is applied in a pan type Hi-coater. The solvent used for forming the wall consists essentially of methylene chloride and methanol 95 parts by weight to 5 parts by weight. A 12 mil, 0.30 mm, thick wall of cellulose acetate butyrate is applied to the exterior surface of the capsule. Finally, an exit means in the form of a passageway is laser drilled through the semipermeable wall communicating with the heat-responsive nutrient containing composition for its delivery to the environment of use.

EXAMPLE 6

Figure 18:
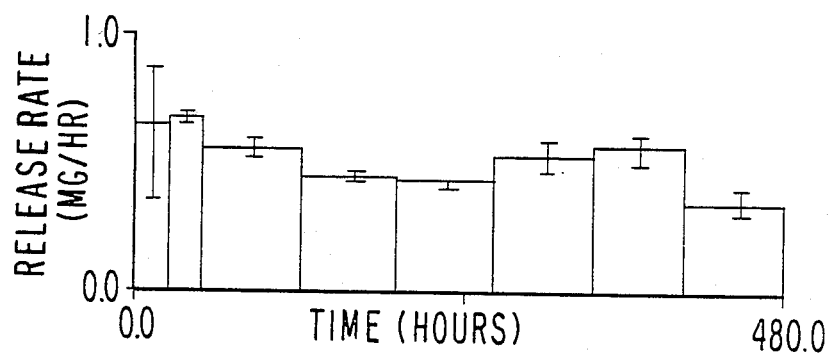
FIG. 18 illustrates the amount of a beneficial agent released over time by a system in vitro as described in Example 6 and provided by the invention; and, FIG. 19 depicts the cumulative amount of a beneficial agent released by a dispensing system in vitro as described in Example 6, over a prolonged period of time.
Figure 19:
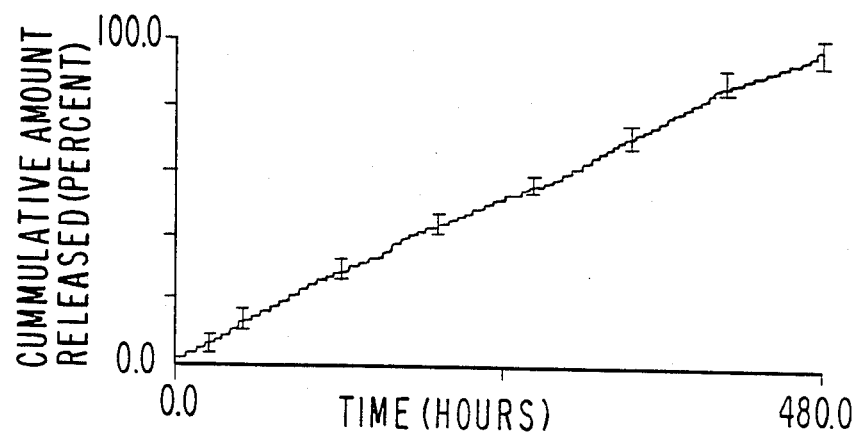

A delivery system is made according to the procedure set forth in Example 1, with the conditions and materials as set forth, except that in this example a varying rate controlling wall thickness comprising a composition of cellulose acetate butyrate and polyethylene glycol 400 is applied to the system. The thickness of the rate controlling wall varies from 30 mil, 0.76 mm, at the end distant from the passageway in a uniform taper to 15 mil, 0.38 mm, adjacent to the density member. Accompanying FIG. 18 depicts the amount of ivermectin antiparasitic released from the system over a prolonged period of 480 hours, and FIG. 19 depicts the cumulative amount of ivermectin released over the 480 hour period. The bars represent the minimum and maximum variation for the release rate at the time of measurement.

EXAMPLE 7

A delivery system is made according to the procedure as set forth in Example 1, with all conditions and materials as previously described, except for the semipermeable wall that comprises 50% cellulose acetate butyrate, 45% poly(sulfone) and 5% citroflex citric acid ester selected from the group consisting of acetyl tributyl citrate and acetyl tri-2-ethylhexyl citrate.

EXAMPLE 8

A delivery system is made according to the procedure as set forth in Example 1, with all conditions as described except that the wall in at least a part comprises 80% cellulose acetate butyrate and 20% poly(sulfone), or the wall comprises 20% cellulose acetate butyrate and 80% poly(sulfone).

EXAMPLE 9

A delivery device manufactured in the shape of an oral dispenser for the controlled delivery of indomethacin is made as follows: First, 300 mg of Butronic ® L-1 polyol, a block polymer formed by the polymerization of 1,2-butylene oxide to which ethylene oxide is added, as reported in *Cosmetics and Toiletries*, Vol. 97, pages 61–66, 1982, which polymer flow at a pour point of 39° C., is melted at 55° C. and then 200 mg of indomethacin is added thereto using a high sheer ultrasonic mixer. The resulting mixture is placed in a vacuum oven at 55° C. and the pressure reduced to less than 10 mm of mercury. The indomethacin Butronic ® composition is allowed to remain in the vacuum for a period of about 10 minutes, for removing entrapped air. Next, 400 mg of the resulting heat-sensitive thermoplastic drug formulation is poured into an opened mouth gelatin capsule. Then, an intermediate lamina forming composition comprising melted paraffin is placed immediately against the heat-sensitive drug formulation. Next, an expandable driving member comprising 100 mg of sodium chloride and 200 mg of the sodium salt of polyacrylic acid available as Carbopol ® 934P is compressed into a tablet. The tablet is formed using a 10 mm tableting tool and 3½ tons of compression force. The tablet has a final shape that corresponds to the internal shape of the opening of the capsule. The tablet member then is inserted into the opened end of the capsule until contact is made with the drug polyol formation. Next, the capsule is coated in a pan coater with a rate controlling wall comprising 1.8 g of 91% cellulose acetate butyrate and 9% polyethylene glycol 400. The wall is coated from a 5% wt/wt solution in methylene chloride methanol 90:10 v/v solvent system. The wall coated delivery systems then are dried at 30° C. for 24 hours. Next, an exit means shaped in the form of a 30 mil exit passageway is drilled through the semipermeable wall using a high speed mechanical drill for communicating with the heat-responsive drug formulation for delivering it from the delivery device.

EXAMPLE 10

A delivery system is made according to the procedure set forth in Example 8, with the conditions as set forth, except that in this example the heat-responsive composition comprises polyethylene glycol 400 distearate, and the expandable-swellable composition comprises 70% by weight of poly(ethylene oxide) having a molecular weight of 3,000,000 and 30% by weight of sodium chloride.

EXAMPLE 11

A dispenser system is prepared as follows: First, the body section of a capsule is positioned with its mouth in an upright position, and then a layer of an expandable-swellable composition is charged into the hemispherical end of the capsule. The composition comprises 25% by weight of the osmotic solute sodium chloride and 75% by weight of the osmopolymer poly(ethylene oxide) having a molecular weight of 200,000. The expandabld forming ingredients are blended in a commercial blender with heat at 30° C. for 20 minutes to yield a homogeneous composition. The heated composition is charged into the capsule forming a layer that occupies about ⅓ of the capsule. Next, a layer of candelilla wax, having a melting point of about 67° C., is placed against the cooled expandable composition. Then, a heat-sensitive drug formulation comprising an eutectic mixture of 77% neutral fat, having a melting point of 35°-37° C., and 19.5% paraffin, having a melting point of 52° C., is heated and 3.5% 2-acetoxybenzoic acid is added thereto. Then, the heated mixture is cooled to about 40° C. and injected into the capsule in contacting relation with the expandable layer, and the capsule allowed to cool to room temperature.

Then, a solution of cellulose acetate, 15 wt %, with an acetyl content of 39.8%, is prepared in a methylene chloride methanol solvent system and the capsule coated with a semipermeable wall. The wall is applied by dipping it into the coating solution 15 times, first for a 5 second dip, then for two 10 second dips, then for a 30 second dip and then for 1 minute per dip, with an intervening 5 minute drying period. Following the dipping the delivery dispenser is dried at room temperature, 72° C., about 22° C., for 5 days. The procedure applies about a 2 mm thick semipermeable wall. A passageway is laser drilled through the semipermeable wall connecting the exterior of the dispenser with the heat sensitive drug formulation for releasing it at a controlled rate over time.

EXAMPLE 12

A dispensing device for delivering a beneficial agent to a warm-blooded animal is prepared as follows: First, a mold is filled with an expandable forming composition comprising 30 parts of ethyleneglycol monomethacrylate containing 0.12 parts of ethyleneglycol dimethacrylate and 10 parts of a 0.13% aqueous solution of sodium disulfate in aqueous ethanol. The composition polymerizes at 30° C., and after 20 minutes following equilibrium to room temperature, the solid layer is removed from the mold. Next, a layer of paraffin having the same shape and size as the expandable composition is placed in laminating arrangement with the expandable composition. Then, a layer of a heat-sensitive carrier comprising cocoa butter plus 2% beeswax and 250 mg of oxprenolol hydrochloride is placed in contacting arrangement with the expandable composition. Then, the laminated arrangement is coated by quick dipping with a wall forming microporous composition consisting essentially of 45% by weight of cellulose acetate having an acetyl content of 39.8%, 45% by weight of sorbitol and 10% by weight of polyethylene glycol 400. Then, a semipermeable wall is coated onto a part of the microporous wall, except for an uncoated drug releasing surface. The semipermeable wall comprises 50% by weight of cellulose acetate having an acetyl content of 39.8% and 50% by weight of cellulose acetate having an acetyl content of 32%.

EXAMPLE 13

A delivery system is made according to the procedure set forth Example 1, with the conditions and materials as set forth, except that in this example the device comprises a single wall of a varying thickness of cellulose acetate butyrate and polyethylene glycol 400. The thickness of the rate controlling wall varied from 30 mil, 0.76 mm, at the end of device 10 to a uniform taper of 15 mil, 0.38 mm, next to the passageway.

An embodiment of the invention pertains to a method of increasing the deliverability of a beneficial agent by formulating a heat-sensitive composition containing a beneficial agent and making the delivery system of the invention for increasing the deliverability of the beneficial agent. An embodiment of the invention pertains also to a method for administering a beneficial drug at a controlled rate orally to an animal, which method comprises the steps of: (A) admitting into the animal a dispensing device comprising: (1) an outer wall comprising in a least a part a semipermeable polymeric composition permeable to the passage of fluid and substantially impermeable to the passage of drug, the wall surrounding (2) an internal lumen containing a layer of a beneficial drug formulation comprising a dosage unit for preforming a therapeutic program in a heat-sensitive pharmaceutically acceptable carrier that melts at body temperature and is a means for transporting the drug from the dispenser; (3) a layer of a means for increasing the deliverability of beneficial agent from the device; (4) a layer of an expandable hydrogel in the lumen; (5) an optional layer of a dense member for maintaining the dispenser in the rumen over a prolonged period of time when the dispenser is administered to a ruminant, and (6) releasing means in the wall communicating with the heat-sensitive drug formulation; (B) imbibing fluid through the semipermeable part of the wall at a rate determined by the permeability of the semipermeable wall and the osmotic pressure gradient across the semipermeable wall and the osmotic pressure gradient across the semipermeable wall causing the layer of expandable hydrogel to expand and swell; (C) melting the drug formulation to form a flowable formulation, and (D) delivering the beneficial drug formulation from the compartment by the expandable layer continually expanding against the intermittent layer and consequently against the melting formulation causing the formulation to be dispensed in a therapeutically effective amount through the exit means at a rate the expansion of the hydrogel, the melting of the formulation and the osmotic properties of the dispenser over a prolonged period of time.

Inasmuch as the foregoing specification comprises preferred embodiments of the invention, it is understood that variations and modifications may be made herein in accordance with the inventive principles disclosed, without departing from the scope of the invention.

We claim:

1. A delivery system for delivering a beneficial agent formulation to an environment of use, the delivery system comprising:
   (a) a wall that surrounds and defines an internal lumen, the wall comprising a semipermeable composition that is permeable to the passage of fluid and substantially impermeable to the passage of a beneficial agent;
   (b) a hydrogel composition in the lumen which expands and occupies an increased volume of the lumen upon imbibing fluid;
   (c) a heat sensitive beneficial agent formulation in the lumen that forms a dispensable formulation at a temperature of at least 25° C.;
   (d) lamina means in the lumen for lessening the incidence of mixing of the heat-sensitive beneficial agent formulation with the hydrogel composition, said lamina means being positioned between the heat-sensitive beneficial agent formulation and the hydrogel composition; and
   (e) means in the delivery system for communicating with the lumen for delivering the beneficial agent formulation to the environement of use over time.

2. The delivery system for delivering the beneficial agent formulation to the environment of use according to claim 1, wherein the means in the delivery system for delivering the beneficial agent comprises at least one passageway.

3. The delivery system for delivering the beneficial agent formulation to the environment of use according to claim 1, wherein the wall that surrounds and defines the internal lumen comprises in at least a part a microporous member.

4. The delivery system for delivering the beneficial agent formulation to the environment of use according to claim 1, where the wall means that surrounds and defines the compartment comprises in at least a part an impermeable member.

5. The delivery system for delivering the beneficial agent formulation to the environment of use according to claim 1, wherein the wall that surrounds and defines the internal lumen comprises a microporous member laminated in part by a semipermeable member.

6. The delivery system for delivering the beneficial agent formulation to the environment of use according to claim 1, wherein the hydrogel composition contains an osmagnet.

7. The delivery system for delivering the beneficial agent formulation to the environment of use according to claim 1, wherein the wall comprises a member selected from the group consisting of a cellulose ester, cellulose diester, cellulose triester, cellulose ether, cellulose ester-ether, cellulose acylate, cellulose diacylate, cellulose triacylate, cellulose acetate, cellulose acetate butyrate, cellulose propionate morpholinobutrate, and cellulose acetate phthalate.

8. The delivery system for delivering the beneficial agent formulation to the environment of use according to claim 1, wherein the delivery system further comprises means in the lumen for maintaining the delivery system in the environment of use over time, said means having a density of at least 1.2.

9. The delivery system for delivering a beneficial agent formulation to the environment of use according to claim 1, wherein the beneficical agent formulation comprises avermectin.

10. The delivery system for delivering a beneficial agent formulation to the environment of use according to claim 1, wherein the beneficial agent formulation comprises ivermectin.

11. The delivery system for delivering a beneficial agent formulation to the environment of use according to claim 1, wherein the heat-sensitive beneficial agent formulation comprises a block copolymer comprising 1,2-butylene oxide and ethylene oxide and ivermectin.

12. The delivery system for delivering a beneficial agent formulation to the environment of use according to claim 1, wherein the heat sensitive beneficial agent formulation comprises a food grade wax and ivermectin.

13. The delivery system for delivering a beneficial agent formulation to the environment of use according to claim 1, wherein the wall comprises cellulose acetate butyrate and polyethylene glycol.

14. The delivery system for delivering a beneficial agent formulaion to the environment of use according to claim 8, wherein the means for maintaining the delivery system in the environment of use comprises a member selected from the group consisting of iron, steel, iron magnesium alloy, and a mixture of cobalt and iron.

15. The delivery system for delivering a beneficial agent formulation to the environment of use according to claim 1, further comprising a body member located between the wall and at least the heat sensitive beneficial agent formulation.

16. The delivery system for delivering a beneficial agent formulation to the environment of use according to claim 15, wherein the body member comprises gelatin.

17. The delivery system for delivering a beneficial agent formulation to the environment of use according to claim 1, wherein the lamina means comprises a single lamina.

18. The delivery system for delivering a beneficial agent formulation to the environment of use according to claim 8, wherein the lamina means comprises a plurality of laminae.

* * * * *